US006881204B1

(12) United States Patent
Bunce

(10) Patent No.: US 6,881,204 B1
(45) Date of Patent: Apr. 19, 2005

(54) CHEST DRAINAGE SYSTEMS

(75) Inventor: Philip Bunce, Portland (AU)

(73) Assignee: Eastland Medical Systems LTD, West Perth (AU)

( * ) Notice: Subject to any disclaimer, the term of this patent is extended or adjusted under 35 U.S.C. 154(b) by 0 days.

(21) Appl. No.: 10/129,024

(22) PCT Filed: Oct. 26, 2000

(86) PCT No.: PCT/AU00/01313

§ 371 (c)(1),
(2), (4) Date: Oct. 15, 2002

(87) PCT Pub. No.: WO01/32233

PCT Pub. Date: May 10, 2001

(30) Foreign Application Priority Data

Oct. 29, 1999 (AU) .................................. PQ3744

(51) Int. Cl.[7] ........................... A61M 1/00; B65D 45/30

(52) U.S. Cl. ..................... 604/326; 604/541; 604/319; 215/276

(58) Field of Search ............................... 604/541, 317, 604/319, 320, 322, 323, 326; 215/276, 311, 215/312, DIG. 3, 129, 388; 141/37; 137/154; 222/400.7

(56) References Cited

U.S. PATENT DOCUMENTS

| 3,090,530 | A | * | 5/1963 | Peeps ....................... 222/400.7 |
| 3,719,197 | A | * | 3/1973 | Pannier et al. .............. 137/205 |
| 4,013,076 | A | | 3/1977 | Puderbaugh et al. |
| 4,993,599 | A | * | 2/1991 | Gruenewald ................ 222/190 |
| 5,045,077 | A | | 9/1991 | Blake, III |
| 5,401,254 | A | * | 3/1995 | Bunce ........................ 604/218 |
| 5,836,483 | A | | 11/1998 | Disel |
| 6,152,902 | A | * | 11/2000 | Christian et al. ........... 604/320 |
| 6,626,668 | B1 | * | 9/2003 | Hubert et al. ................. 433/80 |
| 6,715,624 | B1 | * | 4/2004 | Brockwell .................... 215/247 |

FOREIGN PATENT DOCUMENTS

GB    2 082 071 A    3/1982

* cited by examiner

Primary Examiner—Larry I. Schwartz
Assistant Examiner—Michael G. Bogart
(74) Attorney, Agent, or Firm—Knobbe, Martens, Olson & Bear, LLP

(57) ABSTRACT

A tube connection adapter for coupling one or more tubes of a chest drainage system to a bottle. The adapter has a body adapted to fit onto the mouth of a bottle, the body having an inlet fitting adapted to be connected to a tube of the drainage system to permit entry of fluid into the bottle, and a pressure relief valve adapted to communicate with the interior of the bottle to permit release of pressure in the event of a pressure build-up occurring within the bottle. The pressure relief valve may include a simple ball valve or poppet valve and can be fitted into the adapter body even when there are two or more inlet/outlet fittings.

14 Claims, 3 Drawing Sheets

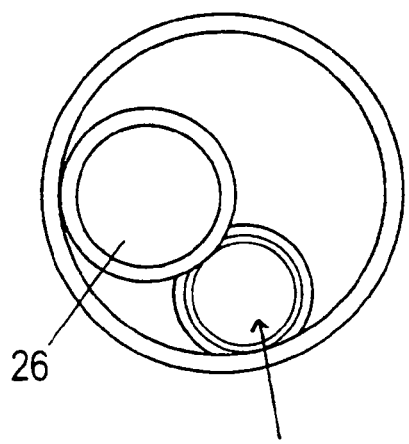
FIG 6A  P
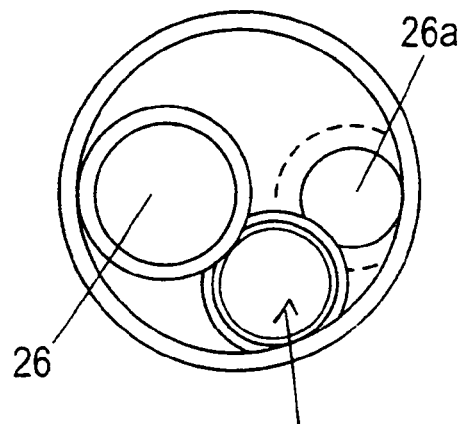
FIG 6B  P
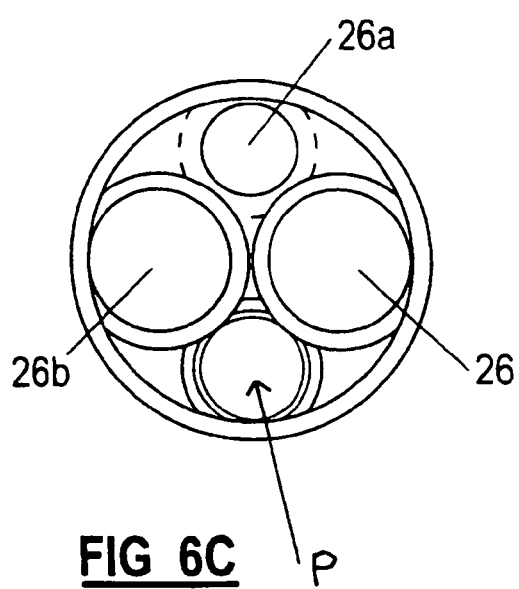
FIG 6C  P
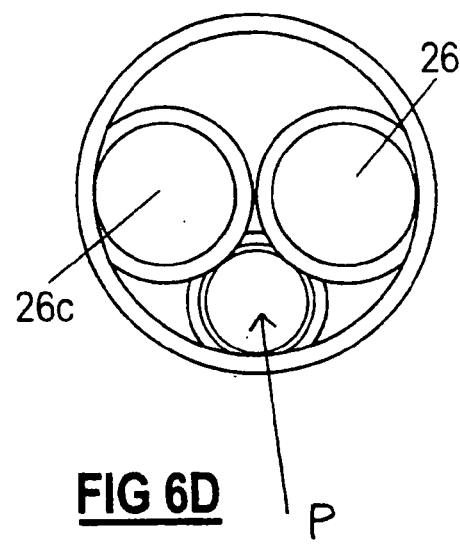
FIG 6D  P

CHEST DRAINAGE SYSTEMS

RELATED APPLICATIONS

This application claims the benefit of the Australian application PQ 3744 filed Oct. 29, 1999 and the international application PCT/AU00/01313 filed Oct. 26, 2000 designating the United States.

BACKGROUND OF THE INVENTION

1. Field of the Invention

The present invention relates to chest drainage systems for draining gas and exudate from a patient following surgery.

2. Description of the Related Art

Chest drainage systems generally include at least one bottle connected to a patient to collect gas and exudate leaking into the thoracic cavity, by allowing drainage to a position lower than the patient while still allowing the patient to breathe. Depending on the needs of a particular patient, chest drainage systems can be set up to operate in different modes. In one mode, drainage can take place by gravity alone and, in other modes, drainage is assisted by the application of external suction by attaching a suction line to the system. A typical chest drainage system will include one, two, or three series—connected bottles depending on the particular set-up. Irrespective of the actual set-up used, one of the bottles will usually include a water seal associated with the inlet tube to that bottle to ensure that air or gas cannot return along the tube once it has bubbled out of the tube; thus the water seal acts as a one-way valve ensuring drainage away from the cavity without permitting air to return. Depending on the set-up used, the system may also have a separate collection bottle and a bottle for controlling the degree of suction.

However, a life-threatening situation can occur if the outlet to one or more of the bottles is closed, for example by being blocked or pinched off whereby the drainage action is restricted with the result that eventually the patient may no longer be able to breathe. This situation is known as pneumothorax. Blockage of an outlet can occur if an outlet tube or suction tube becomes kinked or if a valve linking a suction tube to a suction system is closed without the line being disconnected from the valve.

SUMMARY OF THE INVENTION

According to the present invention, there is provided a tube connection adapter for coupling one or more tubes of a chest drainage system to a bottle, the adapter having a body adapted to fit onto the mouth of a bottle and an inlet fitting adapted to be connected to a tube of the drainage system to permit entry of fluid into the bottle, the body including a pressure relief valve adapted to communicate with the interior of the associated bottle to permit release of pressure in the event of a pressure build-up occurring within the bottle.

As a result of the release of positive pressure, drainage of exudate from the patient can still take place even if an outlet of the system is blocked, thereby reducing the risk of pneumothorax.

When the system is a two- or three-bottle system, the adapter is used with at least the first bottle of the system.

In one embodiment of the invention, a lower part of the adapter body is sized to fit within the mouth of an associated bottle and is bordered by a flange supported by the upper end edge of the mouth of the bottle, the inlet connection fitting of the adapter and the pressure relief valve being incorporated within a zone of the body axially aligned with the lower part thereof to ensure communication with the interior of the bottle.

In one embodiment, the body has at least one further tube connection fitting for example to coupling to an outlet tube and/or a manometer tube. Advantageously, the valve is a simple ball valve, poppet valve, or the like which is closed under the effects of negative pressure within the bottle and which automatically opens under the effects of positive pressure.

In practice, the adapter is secured in its operative position to the mouth of the bottle by a screw-threaded coupling ring rotatably mounted on the body of the adapter.

Further according to the invention there is provided a chest drainage system comprising one or more collection bottles, tubing associated with the bottles for connection to the patient and an adapter as defined above associated with at least the first bottle of the system for coupling the tubing to the bottle.

BRIEF DESCRIPTION OF THE DRAWINGS

Embodiments of the invention will now be described, by way of example only, with reference to the accompanying drawings, in which:

FIGS. 6A to 6D are underneath views of the adapter showing possible positions for the valve in different configurations of inlet and outlet connections.

DETAILED DESCRIPTION OF THE PREFERRED EMBODIMENT

Figure 1:
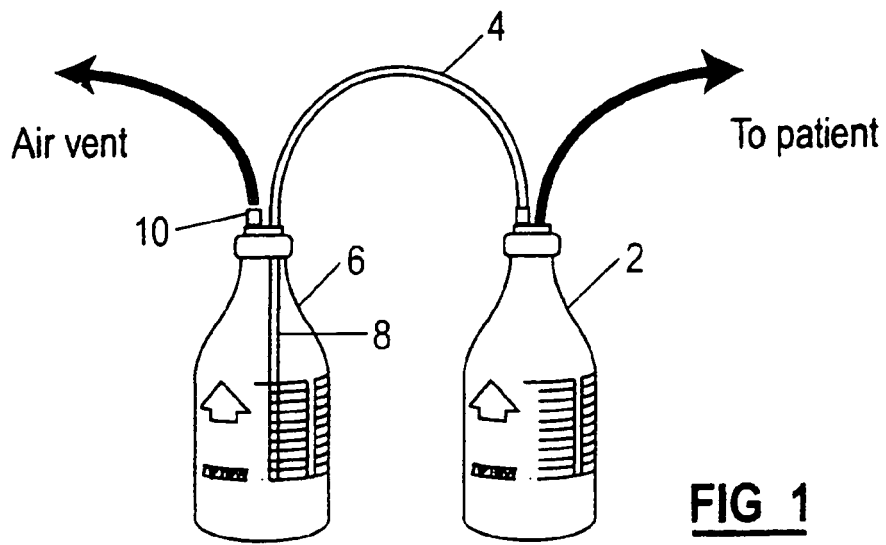
FIG. 1 shows schematically a two-bottle chest drainage system without suction assistance.

FIG. 1 illustrates a typical two-bottle system operating by gravity alone. In this system exudate from the patient drains into the first bottle 2 which is a collection bottle, the first bottle 2 being linked by a flexible tube 4 to a second bottle 6 which forms a water seal using a rigid inlet tube 8 connected to the tube 4 and having a lower end submerged beneath water filling the bottle to a predetermined level. An air vent 10 communicates the interior of the bottle 6 with atmosphere.

A single-bottle gravity system will utilize just the second of the two bottles shown in FIG. 1, with the inlet line 4 being connected directly to the patient. Although a single-bottle gravity system of this type does have the disadvantage that exudate draining into the bottle will progressively raise the level of the water seal within the bottle thereby progressively increasing the resistance of the drainage system, in practice there are situations where this can be tolerated particularly when the rate of discharge of exudate is relatively low.

Figure 2:
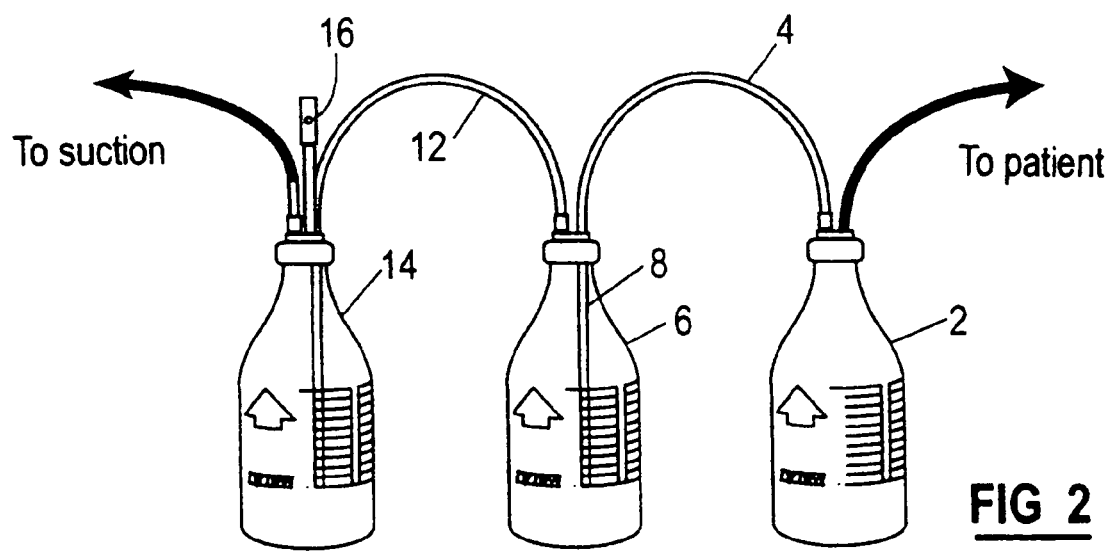
FIG. 2 shows schematically a three-bottle system with suction assistance.

FIG. 2 shows a typical three-bottle system used in a situation where suction assistance is provided. In this system the first and second bottles 2,6 are equivalent to those of the gravity-only system just described except that the outlet from the second bottle 6 is connected by a flexible tube 12 to a third bottle 14 incorporating a manometer tube 16, the outlet from the third bottle 14 being connected to a suction line. The third bottle 14 forms the function of a suction control, the degree of suction being determined by the level of water within that bottle via the manometer tube 16 which is open to atmosphere. A two-bottle system utilizing controlled suction will consist of just the second and third bottles 6,14 just described, with the exudate from the patient draining directly into the bottle 6 which forms the water seal. Although this will result in the level within the water seal bottle progressively rising, the effects of the suction assistance will offset this at least to a degree. The three-bottle system is generally to be preferred in certain applications as the use of the separate collection bottle 2 forming the first of the series of three bottles provides for maximum volume of drained exudate before replacement of the bottle is required and also ensures a constant suction action. Although the systems with suction assistance as described above include two or three bottles having the different functions described, it is also possible to provide a single-bottle system with suction assistance using the second of the two bottles shown. In practice a single-bottle system with suction-assistance does have significant utility in hospitals having a controlled wall suction system when the patient is not subject to excessive bleeding.

Figure 3:
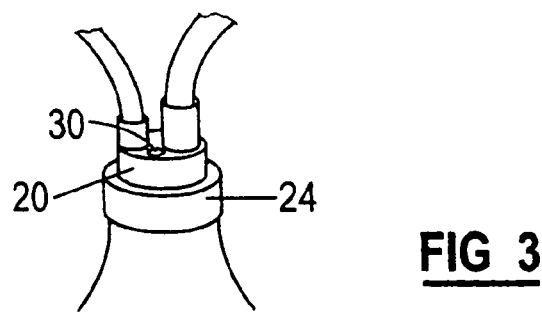
FIG. 3 is a perspective view showing schematically a tube connection adapter in accordance with one embodiment of the invention.
Figure 4:
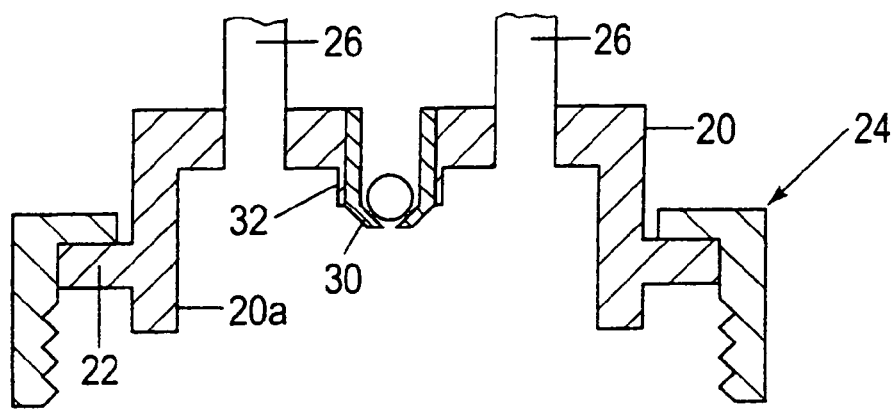
FIG. 4 is a schematic section through the adapter shown in FIG. 3.

In each case the inlet and outlet to each bottle is formed by an adapter 20 (see FIGS. 3 and 4) having an annular flange 22 which rests on the upper edge of the mouth of the bottle, with a lower part 20a of the adapter projecting into the mouth to locate the adapter. The adapter 20 is attached to the bottle by a threaded coupling ring 24 rotatably mounted on the body of the adapter 20 above the flange 22 and having an internally-threaded skirt projecting beneath the flange 22 to engage an external thread of the bottle. The adapter 20 is formed with tubular spigots 26 to which can be attached a flexible inlet tube, a flexible outlet or suction tube, the rigid inlet tube of the water seal or the manometer tube of a suction control, the number of and configuration of the connecting spigots 26 being determined by the particular function the associated bottle is to perform within the drainage system. As will be appreciated, a range of different adapters with different numbers of connecting spigots will be provided to suit the various different set-ups just described. However in each case the inlet/outlet spigots will be configured to lie within a circular zone of a diameter no greater than the internal diameter of the bottle. Advantageously, the adapter 20 and threaded coupling ring 24 is sized to fit onto a bottle having a standardized mouth diameter so that any available bottle having that diameter of mouth can be used in the system.

In accordance with the invention, the adapter 20 for the bottle of a single-bottle system and at least the adapter 20 for the first bottle of a two or more bottle system (the bottle connected to the patient) also includes a simple pressure relief valve 30 to inhibit build-up of pressure within the associated bottle in the event of blockage occurring at the outlet to the bottle in circumstances such as those previously discussed. Accordingly drainage of exudate can still take place thereby reducing the risk of pneumothorax. In a system having two or more bottles the adapter for each bottle may incorporate the pressure relief valve 30.

Figure 5A:
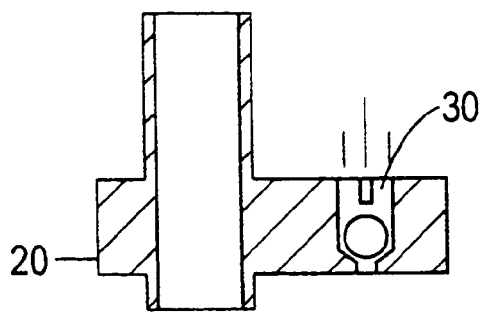
FIGS. 5A to 5D are schematic sections showing different forms of pressure relief valve which can be incorporated within the adapter.
Figure 5B:
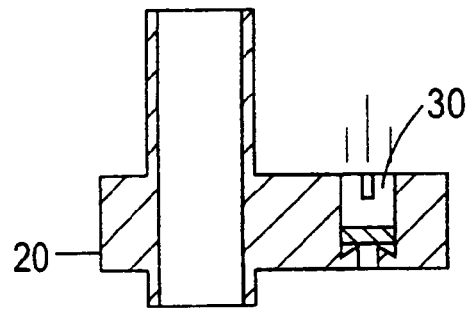
Figure 5C:
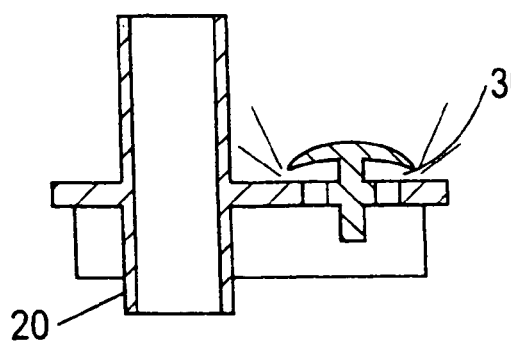
Figure 5D:
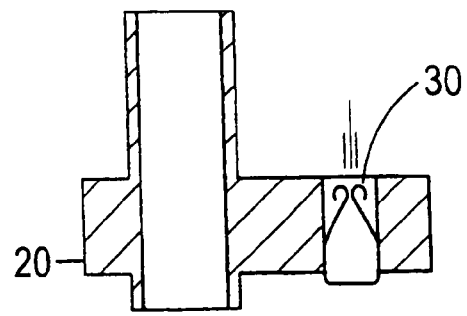

Suitable forms of pressure relief valve 30 are shown schematically in FIGS. 5A to 5D. FIG. 5A shows a ball valve, FIG. 5B shows a poppet valve, FIG. 5C shows an umbrella-type valve, and FIG. 5D shows a duck bill-type valve. In each case the valve 30 is automatically responsive to positive pressure within the associated bottle to automatically open in order to release that pressure and this will ensure that drainage from the patient is not inhibited, while under normal operational conditions the valve will remain closed. For the valves of FIGS. 5A to 5C, the valve member is of light weight and is gravity biased into its closed position in engagement with the valve seat and the effect of any negative pressure within the bottle will be to retain the valve member in the closed position; the valve member will move to an open position even under the effect of small positive pressure. For the valve of FIG. 5D the valve member is subject to an inherent resilient bias which deforms the valve member to a configuration which closes a passage through the valve, the valve member being deformed against the bias under the effect of positive pressure to open the passage. Although the available space in the adapter 20 is restricted, nevertheless there is sufficient space to incorporate the valve 30 within the aforesaid circular zone even in an adapter 20 having three sets of connector spigots 26 as will be described below.

Possible positions P for the valve in relation to the inlet/outlet connector spigots are shown in FIGS. 6A to 6D. FIG. 6A shows the valve position P in an adapter having an inlet spigot 26, with the adapter having an outlet port arrangement such as for use in a single bottle gravity-only system. FIG. 6B shows the valve position P in an adapter having an inlet spigot 26 and a suction outlet 26a. FIG. 6C shows an adapter with an inlet spigot 26, a suction outlet 26a and a fitting for use with a manometer tube 26b and FIG. 6D shows an adapter with an inlet spigot 26, and an outlet or second inlet spigot 26c. The configuration of FIG. 6A is also suitable for use in a single-bottle system with suction assistance, with a suction port being molded into the bottle itself and the configuration of FIG. 6D is suitable for use in a single-bottle system having two patient inlet lines, connected to the spigots 26 and 26c with suction assistance provided by a suction port molded into the bottle itself. This range of configurations is suitable for use with the sole bottle of a single-bottle system either with or without suction assistance, or for use with the first bottle of a two- or three-bottle system either with or without suction assistance.

The adapter 20 is integrally molded in a suitable plastics material and the valve 30 may be incorporated into the adapter 20 by forming within the adapter a suitable socket 32 (see FIG. 4) into which a valve structure consisting of the valve member and valve seat (if applicable) is located.

The adapters described above represent a range of adapters for use with the sole bottle of a single-bottle system either with or without suction assistance or for the first bottle of a two- or three-bottle system either with or without suction assistance. Although it is considered important for the pressure relief function to be applied to the first bottle of a two- or three-bottle system, depending on requirements pressure relief can also be applied to the or each other bottle of the system and the range of adapters described above can also fulfil this function. The pressure relief function provided by each adapter is unaffected by the type of bottle to which the adapter is attached.

The embodiments have been described by way of example only and modifications are possible within the scope of the invention.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

What is claimed is:

1. A tube connection adapter for coupling one or more tubes of a chest drainage system to a bottle, the adapter including:
   a body adapted to fit onto the mouth of a bottle wherein the body includes an annular flange which rests upon the upper edge of the mouth of the bottle;
   a threaded coupling ring positioned outward of the annular flange on the body which extends downward so as to engage threads on the bottle such that tightening engagement of the threaded coupling rings to the threads of the bottle results in the annular flange being urged against the upper edge of the mouth of the bottle;
   an inlet fitting connected to the body and adapted to be connected to a tube of the drainage system to permit entry of fluid into the bottle;
   a pressure relief valve adapted to communicate with the interior of the associated bottle to permit release of pressure in the event of a pressure build-up occurring within the bottle.

2. The adapter of claim 1, wherein a lower part of the adapter body is sized to fit within the mouth of the associated bottle and is bordered by a flange supported by an upper end edge of the mouth of the bottle and wherein the inlet connection fitting and the pressure relief valve are incorporated within a zone of the body axially aligned with the lower part thereof to ensure communication with the interior of the bottle.

3. The adapter of claim 1, wherein the valve is in a closed condition under the effects of negative pressure within the bottle and automatically opens under the effects of positive pressure therein.

4. The adapter of claim 1, further comprising at least one further tube connection fitting adapted for coupling to at least one of an outlet tube and a manometer tube.

5. The adapter of claim 1, further comprising a screw-threaded coupling ring rotatably mounted on the body to secure the adapter to the mouth of the bottle.

6. The adapter of claim 1, wherein the adapter is of molded construction and includes a socket into which the valve is fitted.

7. The adapter of claim 6, wherein the valve comprises a valve body providing a valve seat and a valve member co-operating with the seat to open and close the valve.

8. The adapter of claim 7, wherein the valve member is moved into its closed condition by a gravity bias.

9. The adapter of claim 6, wherein the valve comprises a resilient valve member moved into its closed condition by the inherent resilience of the valve member.

10. A chest drainage system comprising:
    at least a first container for receiving exudate;
    at least a first fluid line transferring the exudate to the at least one container;
    an adapter configured to mate with the at least first container, the adaptor including:
    an annular flange which rests upon the upper edge of the mouth of the bottle;
    a threaded coupling ring positioned outward of the annular ring on the body which extends downward so as to engage threads on the bottle such that tightening engagement of the threaded coupling rings to the threads of the bottle results in the annular ring being urged against the upper edge of the mouth of the bottle;
    an inlet fitting connected to the at least first fluid line; and
    a pressure relief valve communicating with the interior of the at least first container to permit release of pressure in the event of a pressure build-up occurring within the first container.

11. The chest drainage system of 10, further comprising at least a second container and second fluid line and wherein the adapter comprises at least a first outlet fitting communicating with the interior of the first container and wherein the at least second fluid line is attached to the first outlet fitting so as to interconnect the first container and the second container.

12. The system of claim 10, wherein the pressure relief valve maintains positive closure during pressure not exceeding atmospheric within the at least first container and opens upon occurrence of greater than atmospheric pressure within the at least first container.

13. The chest drainage system of claim 10, wherein the system removes exudate under influence of gravity.

14. The chest drainage system of claim 10, wherein the system removes exudate with the assistance of a suction system.

* * * * *

UNITED STATES PATENT AND TRADEMARK OFFICE
CERTIFICATE OF CORRECTION

| | |
|---|---|
| PATENT NO. | : 6,881,204 B1 |
| APPLICATION NO. | : 10/129024 |
| DATED | : April 19, 2005 |
| INVENTOR(S) | : Bunce |

It is certified that error appears in the above-identified patent and that said Letters Patent is hereby corrected as shown below:

Column 6, claim 10, line 17 delete "ring" and insert -- flange--.

Column 6, claim 10, line 20 delete "ring" and insert -- flange --.

Column 6, claim 11, line 28 after "of" insert -- claim --.

Signed and Sealed this

Fourteenth Day of November, 2006

JON W. DUDAS
*Director of the United States Patent and Trademark Office*